United States Patent [19]

Rupchock et al.

[11] 4,447,526

[45] May 8, 1984

[54] HOMOGENEOUS SPECIFIC BINDING ASSAY WITH CARRIER MATRIX INCORPORATING SPECIFIC BINDING PARTNER

[75] Inventors: Patricia A. Rupchock; Richard J. Tyhach, both of Elkhart, Ind.

[73] Assignee: Miles Laboratories, Inc., Elkhart, Ind.

[21] Appl. No.: 255,521

[22] Filed: Apr. 20, 1981

[51] Int. Cl.³ .................... G01N 33/54; G01N 33/58; G01N 33/52

[52] U.S. Cl. ......................................... 435/7; 422/56; 435/805; 436/528; 436/530; 436/535; 436/537; 436/810

[58] Field of Search ............... 435/4, 7, 805, 810; 23/230 B; 424/8, 12; 422/52, 55, 56; 436/514, 515, 516, 531, 532, 536, 537, 538, 528, 530, 535

[56] References Cited

U.S. PATENT DOCUMENTS

| | | | |
|---|---|---|---|
| 3,979,184 | 9/1976 | Giaever | 435/7 |
| 4,059,407 | 11/1977 | Hochstrasser | 435/7 |
| 4,094,647 | 6/1978 | Deutsch et al. | 435/7 |
| 4,226,978 | 10/1980 | Boguslaski et al. | 435/7 |
| 4,238,565 | 12/1980 | Hornby et al. | 435/7 |
| 4,258,001 | 3/1981 | Pierce et al. | 435/7 |
| 4,275,149 | 6/1981 | Litman et al. | 435/7 |
| 4,279,992 | 7/1981 | Boguslaski et al. | 435/7 |
| 4,299,916 | 11/1981 | Litman et al. | 435/7 |
| 4,318,981 | 3/1982 | Burd | 435/7 |
| 4,323,647 | 4/1982 | Monji | 435/7 |
| 4,362,697 | 12/1982 | Tubb et al. | 422/56 |
| 4,363,874 | 12/1982 | Greenquist | 422/56 |
| 4,366,241 | 12/1982 | Tom et al. | 422/56 |
| 4,366,243 | 12/1982 | Rupchock et al. | 435/7 |
| 4,391,904 | 7/1983 | Litman | 435/7 X |

*Primary Examiner*—Sidney Marantz
*Attorney, Agent, or Firm*—Edward H. Gorman, Jr.

[57] ABSTRACT

A method for determining the presence of a ligand in, or the ligand binding capacity of a liquid test sample which includes the steps of (a) adding to the sample a conjugate of the ligand and a label, (b) contacting the sample with a test device containing reagents which in conjunction with the conjugate and ligand, are capable of producing a detectable response, and (c) measuring the response.

16 Claims, 1 Drawing Figure

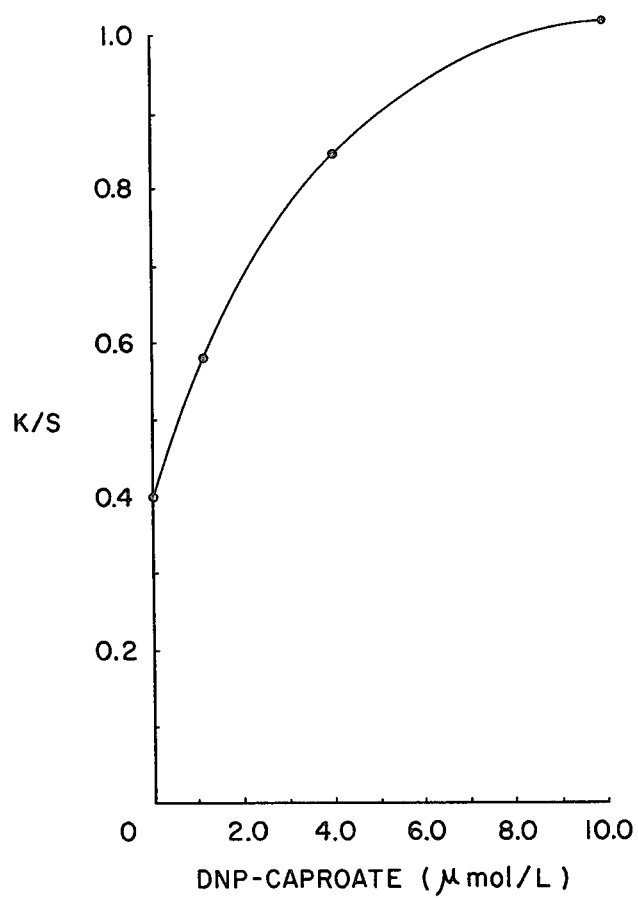

HOMOGENEOUS SPECIFIC BINDING ASSAY WITH CARRIER MATRIX INCORPORATING SPECIFIC BINDING PARTNER

BACKGROUND OF THE INVENTION

1. Field of the Invention

The presently disclosed invention relates to a method for performing an assay in a liquid test sample. It has been discovered that a homogeneous specific binding assay can be performed in a liquid sample using a solid state test device, therefore eliminating the need for preparing solutions of reagents immediately prior to performing the assay.

In addition, the invention relates to a test device which can be stored for long periods of time prior to its ultimate use in performing an assay.

In addition, the invention relates to the stabilization of glucose oxidase apoenzyme compositions which can be used in specific binding assays, such as immunoassays. Such compositions can be used to detect the presence of ligands in, or the ligand binding capacity of, a liquid test sample. They may be used by themselves in wet chemistry procedures, or they can be incorporated with a dry test device format for similar specific binding assays.

Test devices in the form of test strips and similar solid state analytical elements have become commonplace in the analysis of various types of liquid samples such as biological fluids, industrial fluids, and others. Their popularity stems from among other reasons, their convenience and speed. As a result, test strips have been designed for detecting various clinically significant substances in both serum and urine. They have proven to be extremely advantageous in assisting the diagnosis and treatment of disease states in man and animals.

Test strip devices generally comprise a carrier member, such as an absorbent or bibulous matrix, incorporated with reagents which interact with one or more constituents of a liquid test sample to provide a detectable response, such as a color change. The sample under assay is contacted with the reagent-incorporated carrier member, such as by momentarily immersing the device in the sample or by applying to it an aliquot of the sample, and the response is observed after a given time has elapsed. One great advantage of such test devices is the convenience of their routine use. They eliminate such inconvenient, time consuming steps as reagent additions to the sample and provide a rapid, easily observable signal.

Test strips of various types are known for use in a wide variety of fields. They include the familiar pH test paper devices, and a migriad of in vitro diagnostic devices for the detection of various urine and blood components such as glucose, protein, occult blood and so forth (e.g., as described in U.S. Pat. Nos. 3,164,534; 3,485,587; and 3,012,976). Reagent compositions found in such conventional test strips interact with the constituent or constituents to be determined by direct chemical or enzymatic reaction and, for this and other reasons, have limited sensitivity, being applied to the detection of substances that are present in liquid samples at concentrations in the millimolar range or above.

On the other hand, the development of specific binding assay techniques has provided extremely useful analytical methods for determining various organic substances of diagnostic, medical, environmental and industrial importance which appear in liquid mediums at very low concentrations. Specific binding assays are based on the specific interaction between the ligand, i.e., the bindable analyte under determination, and a binding partner such as an antibody. Where one of the ligand or its binding partner is an antibody and the other is a corresponding hapten or antigen, the assay is known as an immunoassay.

In conventional specific binding assay techniques, a sample of the liquid to be assayed is combined with reagent systems of various compositions. Such compositions include a labeled conjugate comprising a binding component incorporated with a label. The binding component in the labeled conjugate participates with other constituents, if any, of the reagent system and the ligand under assay to form a binding reaction system producing two species or forms of the labeled conjugate: a bound-species and a free-species. In the bound-species the binding component in the labeled conjugate, e.g., a hapten or antigen, is bound by a corresponding binding partner (e.g., an antibody) whereas in the free-species, the binding component is not so bound. The relative amount or proportion of the labeled conjugate that results in the bound-species compared to the free-species is a function of the presence (or amount) of the ligand to be detected in the test sample.

Where the labeled conjugate in the bound-species is essentially indistinguishable in the presence of the labeled conjugate in the free-species by the means used to monitor the label, the bound-species and the free-species must be physically separated in order to complete the assay. This type of assay is referred to in the art as "heterogeneous". Where the bound-species and free-species forms of the labeled conjugate can be distinguished in the presence of each other, the separation step can be avoided, and the assay is said to be "homogeneous".

The radioimmunoassay was the first discovered type of highly sensitive specific binding assay to employ a radioactive isotope as the label. Such an assay necessarily must follow the heterogeneous format since the monitorable character of the label is qualitatively unchanged in the free- and bound-species. Because of the inconvenience and difficulty of handling radio-active materials and the necessity of a separation step, homogeneous assay systems have been devised using materials other than radioisotopes as the label component, including enzymes, bacteriophages, metals and organometallic complexes, coenzymes, enzyme substrates, enzyme activators and inhibitors, cycling reactants, organic and inorganic catalysts, prosthetic groups, chemiluminescent reactants, and fluorescent molecules. Such homogeneous specific binding assay systems provide a detectable response, e.g., an electromagnetic radiation signal, such as a color change, chemiluminescence, or fluorescence emission, which is related to the presence or amount of the ligand under assay in the liquid sample.

Commercially available test means for performing specific binding assays are usually in the form of test kits comprising a packaged combination of containers holding solutions or rehydratable compositions of the reagents necessary for carrying out the assay. To perform the actual assay method, aliquots of such solutions must be manually or instrumentally dispensed into a reaction vessel with the sample. If manually dispensed, the assay consequently requires the time and skill of a technician, and if instrumentally dispensed, the assay consequently requires the expense and maintenance of dispensing apparatus.

2. Brief Description of the Prior Art

Solid phase test devices have been applied to heterogeneous specific binding assays in attempts to overcome the inconveniences and disadvantages of the requisite separation step. A commonly used solid phase device of this type comprises a nonporous surface, such as the interior surface of a test tube or other vessel, to which antibody is affixed or coated by adsorption or covalent coupling. U.S. Pat. Nos. 3,826,619; 4,001,583; 4,017,597; and 4.105,410 relate to the use of antibody coated test tubes in radioimmunoassays. Solid phase test devices have also been used in heterogeneous enzyme immunoassays (U.S. Pat. Nos. 4,016,043 and 4,147,752) and in heterogeneous fluorescent immunoassays (U.S. Pat. Nos. 4,025,310 and 4,056,724; and British Patent Spec. No. 1,552,374).

The use of such heterogeneous specific binding assay test devices is exemplified by the method of U.S. Pat. No. 4,135,884 relating to a so-called "gamma stick". The test device is incorporated with the antibody reagent and is brought into contact with the liquid sample and with the remaining reagents of the reaction system, principally the labeled conjugate. After an incubation period, the solid phase device is physically removed from the reaction solution and the label measured either in the solution or on the test device.

Similar devices where the antibody reagent is entrapped in a matrix such as a gel or paper web are described in U.S. Pat. Nos. 3,925,017; 3,970,429; 4,138,474; 3,966,897, 3,981,981 and 3,888,629 and in German OLS No. 2,241,646. Likewise, devices for use in heterogeneous specific binding assays wherein the antibody reagent is fixed to a matrix held in a flow-through column are known (U.S. Pat. Nos. 4,036,947; 4,039,652; 4,059,684; 4,153,675; and 4,166,102). As with all heterogeneous specific binding assay devices, the test device is usually incorporated with less than all of the necessary reagents for carrying out the assay and is merely a means for rendering more convenient the necessary separation step.

Finally, heterogeneous specific binding assay test devices have been described wherein most or all of the necessary reagents are incorporated with the same carrier element, and wherein reagent/sample contacts and separation of the free- and bound-phases are accomplished by capillary migrations along the carrier element (U.S. Pat. Nos. 3,641,235; 4,094,647 and 4,168,146). The devices described in such patents are generally considered difficult to manufacture and susceptible to irreproducibility due to the complex nature of the many chemical and physical interactions that take place along the carrier element during performance of an assay and the low concentrations of ligand or analyte which such devices are intended to determine.

The application of homogeneous specific binding assay reagent systems to solid state test devices would provide great advantages to the routine user of such assay systems. The determination of ligands appearing in very low concentrations in liquid samples would be simplified to the steps of contacting the device with the sample and measuring, either by visual observation or by instrumental means, the resulting signal. Reagents would be provided in a solid form, with no need to store, dispense or mix liquid reagents as is required when using the prior art test kits. Solid state devices would also be much more adaptable to automation than the prior art liquid systems.

The prior art lacks a detailed teaching of how to apply homogeneous specific binding assay reagent systems to solid state test devices. British Patent Spec. No. 1,552,607, commonly assigned herewith, describes homogeneous specific binding assay systems employing various novel labels, including chemiluminescent labels, enzyme substrate labels and coenzyme labels. At page 23, lines 12 et seq of this patent there is the suggestion to incorporate the assay reagents with various carriers including liquid-holding vessels or insoluble, porous, and preferably absorbent, matrices such as bibulous papers; polymeric films, membranes, fleeces, or blocks; gels; and the like.

German OLS No. 2,537,275 describes a homogeneous specific binding assay reagent system and poses the possibility of using slides or strips incorporated with antibody in performing the assay. In this suggestion, the labeled conjugate would be first mixed with the sample and thereafter the antibody incorporated test device contacted with the reaction mixture. After a suitable incubation time, it is proposed that the test device would be rinsed with buffer, dried, and then the signal (fluorescence) measured. Thus, this German OLS poses a test device and assay method much like those already known for heterogeneous specific binding assay techniques wherein the test device is immersed in the liquid reaction mixture, incubated, thereafter removed, washed, and finally read. Additionally, the proposed test device does not incorporate all of the binding assay reagents with the carrier element. Specifically, only the antibody is proposed to be incorporated with the carrier element with the labeled conjugate being separately added to the sample under assay prior to contact with the proposed test device.

SUMMARY OF THE INVENTION

Briefly stated the present invention relates to a method for analyzing a liquid test sample for the presence of a ligand, or for the ligand binding capacity of the sample. The method is performed by sequentially (a) adding to the sample a labeled conjugate comprising the ligand (or its binding analogue) chemically bound to a label, (b) contacting the sample with a test device comprising a carrier matrix incorporated with reagents which, when combined with the labeled conjugate, produce a homogeneous specific binding assay system which produces a detectable response which is a function of the presence of the ligand or ligand binding capacity, thereby producing the detectable response, and (c) measuring the response.

BRIEF DESCRIPTION OF THE DRAWINGS

The FIGURE portrays graphically the data obtained in the experiments described, infra in the Example.

DETAILED DESCRIPTION OF THE INVENTION

The present invention provides a method for using (a) a labeled conjugate comprising a ligand or its specific binding analogue chemically bound to a label, and (b) a test device for use in carrying out homogeneous, non-radioisotopic, specific binding assays containing reagents which, when combined with the conjugate, form a homogeneous specific binding assay reagent system, e.g., immunoassays. As in the case conventional test strip devices, the device used in the present process comprises a solid carrier, usually a matrix of one sort or another, incorporated with all of the reagents necessary to perform a given assay with the exception of the labeled conjugate, whereby the user has only the task of adding the conjugate, bringing the test device into contact with the sample to be tested and measuring the resulting response. Where the entire process is automated, an instrument for performing the same manipulations can have a much simpler design than one having to deal with conventional liquid chemistry systems now used for performing homogeneous specific binding assays.

HOMOGENEOUS SPECIFIC BINDING ASSAYS

Reagents for any homogeneous specific binding assay system may be utilized in the present method. In general, homogeneous specific binding assay techniques are based on the special interaction between (1) a conjugate of a binding component and a label and (2) a binding partner to the binding component in the conjugate, whereby a characteristic of the label is different when the labeled conjugate is bound by the binding partner compared to when such conjugate is not so bound. The affected characteristic of the label may be of any measurable nature, for instance, a chemical or physical quality of the label. In some cases, the affected characteristic is a chemical reactivity in a predetermined reaction which involves the formation or breaking of chemical bonds, covalent or noncovalent. In other cases, the affected characteristic is a physical characteristic of the label which can be measured without chemical reaction.

In the majority of cases, the present test device will incorporate homogeneous specific binding assay reagents which interact with the ligand or its binding capacity in the presence of the conjugate in the sample in an immunochemical manner. That is, there will be an antigen-antibody or hapten-antibody relationship between reagents and/or the ligand or its binding capacity in the sample. Such assays therefore are termed immunoassays and the special interaction between the labeled conjugate and its binding partner is an immunochemical binding. Thus, in such instances, the binding component of the labeled conjugate is an antigen, hapten or antibody (or a fragment thereof) and the binding partner is its corresponding immuno-chemical binding partner. However, it is well understood in the art that other binding interactions between the labeled conjugate and the binding partner serve as the basis of homogeneous specific binding assays, including the binding interactions between hormones, vitamins, metabolites, and pharmacological agents, and their respective receptors and binding substances.

Where the sample is being assayed to determine the presence or amount of a particular ligand therein, the reagents for the homogeneous specific binding assay technique comprise, in the usual case, (1) a labeled conjugate composed of the ligand, or a binding analog thereof, chemically coupled to the label, (2) a binding partner for the ligand, e.g., an antibody or fragment thereof, a natural receptor protein, and the like, and (3) any ancillary reagents necessary for measuring the labeling substance in the labeled conjugate. A limiting amount of the binding substance is introduced so that any ligand in the sample will compete with the labeled conjugate for binding to the binding partner. The distribution of the label between the bound-species and the free-species will therefore determine the magnitude of the detectable response from the label, which in turn will be a function of the presence of the ligand. Another scheme for determining a ligand is presented where the labeled conjugate is composed of a labeled binding partner of the ligand and upon binding to the ligand the label is affected in terms of its detectable response. Where ligand binding capacity of the sample is under assay, the labeled conjugate will be composed of the ligand, or a binding analog thereof, chemically coupled to the label whereby the capacity of the sample to bind the labeled conjugate, such as due to the presence of a binding partner of the ligand in the sample, determines the effect made on the detectable signal from the label.

In the present system, the label is flavin adenine dinucleotide (FAD), the prosthetic group of glucose oxidase, and the ability of the catalytically inactive apoenzyme to combine with its prosthetic group label to form active glucose oxidase is affected by binding of the labeled conjugate with its binding partner.

LIGAND

The present assay may be applied to the detection of any ligand for which there is a specific binding partner and, conversely, to the detection of the capacity of a liquid medium to bind a ligand (usually due to the presence of a binding partner for the ligand in the medium). The ligand usually is a peptide, polypeptide, protein, carbohydrate, glycoprotein, steroid, or other organic molecule for which a specific binding partner exists in biological systems or can be synthesized. The ligand, in functional terms, is usually selected from the group comprising antigens and antibodies thereto; haptens and antibodies thereto; and hormones, vitamins, metabolites and pharmacological agents, and their receptors and binding substances. Usually, the ligand is an immunologically-active polypeptide or protein of molecular weight between 1,000 and 10,000,000, such as an antibody or antigenic polypeptide or protein, or a hapten of molecular weight between 100 and 1,500.

Representative polypeptide ligands are angiotensin I and II, C-peptide, oxytocin, vasopressin, neurophysin, gastrin, secretin, bradykinnin, and glucagon.

Representative protein ligands include the classes of protamines, mucoproteins, glycoproteins, globulins, albumins, scleroproteins, phosphoproteins, histones, lipoproteins, chromoproteins, and nucleoproteins. Examples of specific proteins are prealbumin, $\alpha_1$-lipoprotein, human serum albumin, $\alpha_1$-glycoprotein, transcortin, thyroxine binding globulin, haptoglobin, hemoglobin, myoglobin, ceruloplasmin, $\alpha_2$-lipoprotein, $\alpha_2$-macroglobulin, $\beta$-lipoprotein, erythropietin, transferrin, homopexin, fibrinogen, the immunoglobulins such as IgG, IgM, IgA, IgD, and IgE, and their fragments, e.g., $F_c$ and Fab, complement factors, prolactin, blood clotting factors such as fibrinogen, thrombin and so forth, insulin, melanotropin, somatotropin, thyrotropin, follicle stimulating hormone, leutinizing hormone, gonadotropin, thyroid stimulating hormone, placental lactogen, intrinsic factor, transcobalamin, serum enzymes such as alkaline phosphatase, lactic dehydrogenase, amylase, lipase, phosphatases, cholinesterase, glutamic oxaloacetic transaminase, glutamic pyruvic transaminase, and uropepsin, endorphins, enkephalins, protamine, tissue antigens, bacterial antigens, and viral antigens such as hepatitis associated antigens (e.g., $HB_sAg$, $HB_cAg$ and $HB_eAg$).

Representative hapten ligands include the general classes of drugs, metabolites, hormones, vitamins, and the like organic compounds. Haptenic hormones include thyroxine and triiodothyronine. Vitamins include vitamins A, B, e.g., $B_{12}$, C, D, E and K, folic acid and thiamine. Drugs include antibiotics such as aminoglycosides, e.g., gentamicin, tobramycin, amikacin, sisomicin, kanamycin, and netilmicin, penicillin, tetracycline, terramycin, chloromycetin, and actinomycetin; nucleosides and nucleotides such as adenosine diphosphate (ADP), adenosin triphosphate (ATP), flavin mononucleotide (FMN), nicotinamide adenine dinucleotide (NAD) and its phosphate derivative (NADP), thymidine, guanosine and adenosine; prostaglandins; steroids such as the estrogens, e.g., estriol and estradiol, sterogens, androgens, digozin, digitoxin, and adrenocortical steroids; and others such as phenobarbital, phenytoin, primidone, ethosuximide, carbamazepine, valproate, theophylline, caffeine, propranolol, procainamide, quinidine, amitryptiline, cortisol, desipramine, disopyramide, doxepin, doxorubicin, nortryptiline, methotrexate, imipramine, lidocaine, procainamide, N-acetyl-procainamide, the amphetamines, the catocholamines, and the antihistamines.

The liquid medium to be assayed can be a naturally occurring or artificially formed liquid suspected to contain the ligand, and usually is a biological fluid or a dilution thereof. Biological fluids that can be assayed include serum, plasma, urine, saliva, and amniotic and cerebrospinal fluids.

CARRIER MATRIX

The carrier matrix of the present invention can take on a multitude of forms, and is therefore intended as being broad in context. It can be mono- or multiphasic, comprising one or more appropriate materials or mediums of similar or different absorptive or other physical characteristics. It can be hydrophobic or hydrophilic, bibulous or nonporous. In its most efficient embodiment the carrier member can be carefully tailored to suit the characteristics of the particular homogeneous specific binding assay system to be employed.

Thus, as used herein, the term "carrier matrix" can comprise any substance capable of being incorporated with specific binding assay reagents. It can take on many known forms such as those utilized for chemical and enzymatic reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British patent, No. 1,349,623, suggests the use of a light-permeable meshwork of thin filaments as a cover for an underlying paper carrier element. This reference also suggest impregnating the paper with part of a reagent system and impregnating the meshwork with other potentially incompatible chemical or enzymatic reagents. French Pat. No. 2,170,397 teaches the use of carrier matrices having greater than 50% polyamide fibers therein. Another approach to carrier matrices is disclosed in U.S. Pat. No. 4,046,513 wherein the concept of printing reagents onto a suitable carrier is employed. U.S. Pat. No. 4,046,514 discloses the interweaving or knitting of filaments bearing reagents in a reactant system. All such carrier matrix concepts can be employed in the present invention, as can others. Preferably the carrier matrix comprises a bibulous material, such as filter paper, whereby a solution or suspension of the reagents of the specific binding assay system is used to impregnate the carrier matrix. It can also comprise a system which physically entraps the ingredients, such as in polymeric microcapsules, which then rupture upon contact with the test sample. It can comprise a system wherein the ingredients are homogeneously combined with the carrier matrix in a fluid or semi-fluid state, which later hardens or sets, thereby entrapping the ingredients.

Whichever material is chosen for the carrier matrix, whether it be porous to permit incorporation of ingredients such as through saturation with a solution containing them, whether it be nonporous such as for use in printed application of reagents or to support a continuous coating, whether it be woven or knitted, whatever its composition or configuration, its selection will in any event be dictated by anticipated use and by the reagent system. For example, it may be desirable to utilize a multi-step application of reagents. In such a case, two or more solutions or suspensions of reagents are prepared, the carrier matrix being dipped sequentially into each with drying steps between dippings. In such a case a porous material such as paper might be most advantageous. Alternatively, it might be desirable to utilize a multiphasic carrier matrix, where two or more layers of porous material are affixed one atop another. Still another approach to carrier matrix incorporation is to sequentially coat a continuous polymer with coatings containing different reagents of the immunoassay system. Filtering layers can be present in the carrier matrix to preclude potential interfering agents from reaching the assay system, while permitting access to any analyte present in the sample.

Thus, it can be seen that proper selection of the carrier matrix is dependent on only two factors:

anticipated use and the nature of the specific binding assay system to be employed. Given the present teachings, it becomes a matter of routine experimentation to select the proper carrier matrix.

PREPARATION OF THE TEST DEVICE

Many ways exist of incorporating the assay composition of the present invention with a carrier matrix, and some of these are exemplified by the patents cited in the previous section entitled "Carrier Matrix".

These methods include: the printing of solutions or suspensions of the composition into a printable surface; coating, as with a doctor blade, brush or sprayer; and immersion of a porous matrix into a solution or suspension of the assay composition, followed by drying. Preferably, a two-dip process is employed, whereby a strip of filter paper is thoroughly wetted with a solution of an oxidation-reduction indicator such as 3,3',5,5'-tetramethylbenzidine, followed by drying and subsequent wetting of the remainder of the reagents making up the assay composition. Other preparations will be apparent to those of reasonable skill, especially in view of the Examples, infra.

DETECTABLE RESPONSE

As previously noted, many of the recently devised homogeneous specific binding assay systems provide, or can be readily adapted to provide, a detectable response such as a color change, chemiluminescence, or fluorescence related to the presence or amount of the ligand under assay in the liquid sample. Examples are electromagenetic radiation signals such as fluorescence, phosphorescense, chemiluminescence, a change in light absorption, or reflectance in the visible spectrum thereby producing a visible color change, a change in light absorption or reflectance outside the visible range such as the ultraviolet or infrared. As will be apparent to one skilled in the art of immunoassays, the phrase "detectable response", as used herein, is intended in its broadest sense.

EXAMPLE

The following examples describe experiments which were performed in developing the present invention. While it illustrates preferred embodiments, it is in no way to be interpreted as limiting the scope of the invention.

In order to study various parameters of incorporating the prosthetic group label homogeneous immunoassay reagent system described in British Pat. No. 2,023,607 into a dry test device format, a model system was experimentally devised. The ligand to which the model system was responsive was N-(2,4-dinitrophenyl)-ε-aminocaproic acid (hereafter "DNP-caproate"). Reagents comprising the immunochemical components of the system included antibody to the 2,4-dinitrophenyl moiety (DNP), a conjugate of DNP and flavin adenine dinucleotide (hereafter "DNP-FAD"), and apoglucose oxidase.

The system was designed to respond to DNP by exhibiting color due to the activation of apoglucose oxidase by the DNP-FAD conjugate. DNP-FAD which does not become bound by antibody is directly proportional to DNP concentration. It is detectable by its ability to combine with apoglucose oxidase to produce active glucose oxidase enzyme. Thus the response system included, in addition to apoenzyme, antibody and conjugate, a glucose oxidase detection system comprising glucose, 3,3',5,5'-tetramethylbenzidine (TMB), and horseradish peroxidase. Upon activation of the apoenzyme to glucose oxidase, a blue color formed due to the oxidation of glucose to hydrogen peroxide and subsequent conversion of TMB to its blue oxidized state in the presence of peroxidase.

1. Preparation of Apoenzyme

Apoenzyme was prepared from a sample of highly purified glucose oxidase obtained from Miles Laboratories, Inc. (Catalog No. 31-619). 10.5 milliliters (ml) of this enzyme solution (1000 units/ml) was mixed in a glass beaker with 4.5 ml of glycerol, and the mixture was cooled to a temperature of 0°–4° C. The pH of the mixture was lowered, using a 10% aqueous solution of sulfuric acid, until a pH of 1.4 was reached. This procedure was carried out with constant stirring with the beaker immersed in an ice bath, and the stirring was continued for 2 hrs. After that time, the solution was poured over a 1.5 by 43 centimeter (cm) column of Sephadex G-50 (medium) cross-linked gel filtration media. The Sephadex had been equilibrated previous to the introduction of the enzyme solution with a 30% by volume aqueous glycerol solution having a pH of 1.4. Following the introduction of the enzyme solution onto the Sephadex column, more of the 30% glycerol solution was used to elute apoenzyme. The effluent was separated into fractions and observed using UV absorbance at 280 nanometers (nm). Those fractions having absorbance at this wavelength were combined with a buffer solution containing 50 milligrams (mg) of activated charcoal and 25 mg of dextran (Pharmacia Company No. T-70). The buffer comprised an aqueous solution which was 1 molar (M) tris(hydroxymethyl)aminomethane to which glutamic acid was added until a MS-1175 pH of 7.0 was reached. The pH of the resultant effluent solution was then readjusted to 7 using a saturated solution of tris(hydroxymethyl)aminomethane. This final solution was allowed to stir in an ice bath for 1 hr. The apoenzyme solution was then centrifuged and the supernatant was filtered through 0.5 micrometer (μm) and 0.22 μm filters obtained from Millipore Corporation.

2. Preparation of DNP-FAD Conjugate

The conjugate was prepared as follows. $N^6$(Trifluoroacetamidohexyl)adenosine-5'-monophosphate was synthesized by the method of Trayer et al., Biochem. J., 139, 609–623 (1974). Fifty-six mg. of $N^6$-(trifluoroacetamidohexyl)adenosine-5'-monophosphate [(0.1 millimoles (mmol)] was dissolved in about 10 ml of water, and 25 microliters (μl) of tri-n-butylamine (0.1 mmol) was added. The water was removed under vacuum, and the residue was dissolved in 10 ml of dry dimethylformamide which was then removed under vacuum. The residue was evaporated from dry dimethylformamide three more times. The final residue was dissolved in 10 ml of dry dimethylformamide. Eight mg. of N,N' carbonyldiimidazole (0.5 mmol) was added and allowed to react for 1.5 hrs. The 15 μl water was added and the solvent was removed under vacuum. The residue of $N^6$-(trifluoroacetamidohexyl)adenosine-5'-monophosphate imidazolide was dissolved in 10 ml of dimethylformamide.

Forty-seven milligrams of riboflavin-5'-monophosphate (0.1 mmol), purified by the method of Johnson et al., Anal. Biochem., 86, 526–530 (1978), was dissolved in about 10 ml of water and added dropwise to 20 ml of acetone containing 43 μl of tri-n-octylamine (0.1 mmol). A precipitate formed before the addition was complete. The solvent was removed with a rotary evaporator until the riboflavin-5'-monophosphate dissolved. Then 5 ml of acetone and 5–10 ml of dimethylformamide were added and the mixture taken to dryness. The residue was dissolved in 15 to 20 ml of dry dimethylformamide and taken to dryness. This procedure was repeated three times. The residue was dissolved in 5 ml dimethylformamide and combined with the above-mentioned 10 ml of solution of the imidazolide in dimethylformamide. The reaction mixture was allowed to stand at room temperature overnight and then the solvent was removed. The residue was taken up in 50 ml of water and applied to a 2.5×25 cm column of DEAE-cellulose (Whatman DE 23; Whatman, Inc., Clifton, N.J.) in the bicarbonate form. The chromatogram was developed with a linear gradient generated with 2 liters of water and 2 liters of 0.3 M-ammonium bicarbonate (23 ml fractions were collected). Thin-layer chromatography on silica gel 60-F254 (E. Merck, Darmstadt, West Germany), using ethanol/1 M triethylammonium bicarbonate pH 7.8 (7:3, by volume), showed that fractions numbered 68 to 73 contained major ($R_F$ 0.75) and minor ($R_F$ 0.36) yellow compounds. These fractions were pooled, and the optical adsorption spectrum had maxima at 267 nm, 373 nm, and 450 nm.

The solvent was removed from the pooled material, and the residue was dissolved in about 5 ml of water. This solution was adjusted to pH 11.0 with 5 M NaOH and allowed to stand at room temperature for 9 hrs. Thin-layer chromatography showed that the component with $R_F$ 0.75 disappeared while a new yellow material with $R_F$ 0.37 appeared. The reaction mixture was adjusted to pH 8.0 with hydrochloric acid and applied to a column (2.5×20 cm) of DEAE-cellulose in the bicarbonate form. The chromatogram was developed with a linear gradient of 1 liter of water and 1 liter of 0.2 M-ammonium bicarbonate. The yellow effluent from the column was pooled and the solvent was removed. The residue was adsorbed onto 2 g of silica gel which was placed atop a 50 g column of silica gel equilibrated with ethanol/1 M triethylammonium bicarbonate, pH 7.8 (8:2 by volume). The chromatogram was developed with the same solvent, the yellow component with $R_F$ 0.37 was collected, and the solvent was removed. The yield of flavin $N^6$-6-N-aminohexyladenine dinucleotide [hereinafter $N^6$(aminohexyl)FAD] based on absorbance at 450 nm was about 10%.

To 10 ml of 0.21 M aqueous sodium bicarbonate containing 0.06 millimoles of $N^6$(aminohexyl)FAD was added dropwise 17 µl of 2,4-dinitrofluorobenzene (0.13 nmol) in one ml of absolute ethanol with stirring. The reaction mixture was stirred in the dark for four to six hours and then 10 µl of 2,4-dinitrofluorobenzene (0.08 mmol) dissolved in 0.5 ml of ethanol was added. The reaction mixture was stirred overnight. Thin-layer chromatography on silica gel (silica gel 60, F-254, E. Merck) using an ethanol/1 M triethylammonium bicarbonate, pH 7.5, (7:3) solvent showed that the $N^6$(aminohexyl)FAD had completely reacted.

The reaction mixture was filtered through Whatman #1 paper and the filtrate was applied to a 2.5×56 cm column of Sephadex LH-20 which was equilibrated with 0.3 M ammonium bicarbonate. The chromatogram was developed with this solvent and several yellow materials were eluted as separate peaks. The peak eluted between 470 and 590 ml of 0.3 M ammonium bicarbonate was the only one which activated apoglucose oxidase. Thin-layer chromatography as described above resolved this material into two yellow fluorescent spots with $R_f$=0.84 and 0.89. The optical absorption spectrum had maxima at 265, 370 and 455 nm.

A sample of the product was allowed to react with a snake venom phosphodiesterase preparation (Crotalus adamanteus) obtained from Worthington Biochemical Corp. Thin-layer chromatography showed that the reaction products were riboflavin-5'-monophosphate and $N^6$(2,4-dinitrophenylaminohexyl)adenosine-5'-monophosphate, as expected.

3. Preparation of Test Device

The device was prepared by incorporating the ingredients into a paper carrier matrix in a two-dip process. The first impregnation dip was an acetone solution made 2 mM in TMB. Pieces of Eaton & Dikeman 205 filter paper measuring 4 cm square were dipped into the TMB solution (first-dip), removed, and dried in a forced air oven at 90° C. for 1-2 minutes.

A second-dip solution was prepared by combining the following ingredients in the order listed:

| | |
|---|---|
| Aqueous Buffer (pH 6.4)* | 0.4 ml |
| Glucose (1 M) 0.2 ml | |
| Horseradish Peroxidase (153 units/mg; 1.25 mg/ml) | 0.2 ml |
| Polyvinyl Alcohol (Monsanto 20-30; 10 gm/100 ml water) | 0.2 ml |
| Bovine Serum Albumin (Miles Laboratories, Inc.; 20 mg/ml of water) | 0.05 ml |
| Apoglucose Oxidase (5.0 nanomoles FAD binding sites/ml) | 0.4 ml |
| Partially purified antibody to DNP** | 0.56 ml |

*The Buffer comprises an aqueous solution of 10.8 grams (g) of tris-(hydroxymethyl) aminomethane, 9.7 g glutamic acid and 1.6 g citric acid per 100 ml of solution.
**Partially purified antibody was prepared from a DNP antiserum obtained from Miles Laboratories, Inc. The immunoglobulin fraction was isolated by precipitation with ammonium sulfate as described by Livingston in "Methods, in Enzymology", vol. XXXIV) W.B. Jakoby and M. Wilchek, 3ds.) p 725, Academic Press (New York, 1974). The final precipitate from this procedure was dissolved in 50 mM potassium phosphate (pH 6.8) to bring the total volume to the original volume of serum used. This solution was dialyzed overnight at 4° C. against 500 volumes of the same buffer (50 mM potassium phosphate).

Prior to use in the present experiment, the apoenzyme solution prepared as above was dialyzed against 20 mM tris-glutamate buffer at a pH of 7.0 and which contained 10% by weight of mannitol.

This second dip solution was then used to impregnate the papers which had previously been impregnated with TMB. The TMB-bearing papers were dipped into the second-dip solution, removed, and dried in a forced air oven at 90° C. for six minutes.

Test devices were prepared having 0.5 cm squares of the dried paper mounted at one end of biaxially oriented polystyrene strips measuring about 0.5×8.3 cm. The mounting was achieved using a double-face adhesive tape available from the 3M company and known as Double-Stick.

The reagent system was completed by contacting the reagent device as prepared above with aqueous solutions which were made 1 µM in DNP-FAD conjugate. All of the solutions utilized in testing the devices contained that amount of conjugate and either none or varying amounts of the ligand, DNP-caproate. Accordingly, four test solutions were made up as follows:

| Test Solution | Contents |
|---|---|
| 1 | 1 µM DNP-FAD |
| 2 | 1 µM DNP-FAD and 1 µM DNP-Caproate |
| 3 | 1 µM DNP-FAD and 4 µM DNP-Caproate |
| 4 | 1 µM DNP-FAD and 10 µM DNP-Caproate |

4. Performance Evaluation

In examining the performance of the test devices, each was wet with 15 µl of one of the above test solutions. After being contacted with the test solution, each device was incubated for 6 minutes in a covered petri dish having a wetted piece of filter paper in the bottom. This served as a humidity chamber.

The performance of the reagent devices prepared and incubated as above-described was analyzed instrumentally using a device known as the "Rapid Scanner". This device is a scanning reflectance spectrophotometer interfaced with a PDP-12 computer obtained from the Digital Equipment Corporation. The instrument is used for the rapid measurement of reflectance spectra in the visual range. The computer allows for the storage of spectral data and computations. Measurements of the performances of reagents strips in the Rapid Scanner have the following advantages over visual observations of the same devices:

1. The light source and conditions surrounding the sample remains fixed. In visual readings the light source can vary, not only in wavelength components, but also in relation to the locations of the strips being observed.

2. The detector characteristics remain fixed in the Rapid Scanner. In visual observation, the detector (i.e. in the eyes of the observer) varies from person to person and, with the same person, from day to day.

3. The Rapid Scanner allows more precise quantitation of the data then does human observation, thereby permitting comparisons between the results to be made in a more objective manner than with visual observation.

The Rapid Scanner instrument was constructed by the Ames Company Division of Miles Laboratories, Inc., Elkhart, Ind. U.S.A., from whom complete information with respect to structural and performance characteristics are obtainable.

Test devices which had been inoculated with the four solutions were analyzed using the Rapid Scanner. The reflectance data obtained at 660 nm, which is the maximum absorption wavelength in the blue color range of oxidized TMB, is respresented graphically in FIG. I, wherein K/S is plotted against DNP-caproate concentration.

K/S is defined as follows:

$$K/S = (1-R)^2/2R$$

in which K is a constant, S is the scattering coefficient of the particular reflecting medium, and R is the fraction of reflectance from the test strip. This relationship is a simplified form of the well-known Kubelka-Munk equation (Gustav Kortüm, "Reflectance Spectroscopy", pp. 106–111, Springer-Verlaz, New York (1969).

K/S is a function of the colorant concentration. It increases with increasing ligand concentration, thereby indicating the efficacy of the device in quantitatively analyzing solutions of varying concentrations of DNP-caproate.

The results from the Rapid Scanner were also used to assess performance by calculating color difference units ($\Delta E$) which are presented in the Figure. $\Delta E$ is a value which is proportional to the appearance of color as a result of the presence of apoenzyme and the DNP-FAD conjugate together with the indicator, peroxidase and glucose present in the test device. Tristimulus values from the Rapid Scanner are used to calculate $\Delta E$ according to the convention described in "Supplement No. 2 to Commission International de L'Eclairage (Paris), Publication No. 15, Colorimetry, (E.-1.3.1), 1971."

The $\Delta E$ values tabulated in the Figure show that the differences in color with respect to each of the ligand solutions were large enough to enable visual correlation between the color of the test device and the concentration of ligand.

This experiment demonstrates the practicality of mixing and storing the reagents of an immunochemical assay system long before the time of actual performance of the assay. It also proves the efficacy of ligand analysis using the technique of adding the ligand-label conjugate to the sample and subsequently contacting the sample with a test device containing the remainder of the reagents for the homogeneous specific binding assay.

What is claimed is:

1. A method for determining the presence of a ligand in, or the ligand binding capacity of a liquid test sample, the method comprising the steps of forming a solution or suspension of a labeled conjugate and the liquid sample, the conjugate comprising the ligand or a specific binding analog of the ligand and a label, whereby a characteristic of the label is different when the conjugate is bound by a specific binding partner for said ligand or analog, compared to when said conjugate is not so bound, said difference in said characteristic being detectable, contacting said sample with a carrier matrix incorporated with reagents which, when in the presence of said conjugate, produce a homogeneous specific binding assay system wherein said difference in said label characteristic is detectable, said reagents comprising said specific binding partner, thereby producing said difference in said characteristic, and measuring said difference.

2. The method of claim 1 wherein said difference is measured by human observation.

3. The method of claim 1 wherein said difference is measured by instrumental means.

4. The method of claim 1 wherein said carrier matrix comprises a substance absorbent to said liquid sample.

5. The method of claim 1 wherein said carrier matrix is paper.

6. The method of claim 1 wherein said carrier matrix comprises a polymeric film or gel.

7. The method of claim 1 wherein said label participates in an enzymatic reaction.

8. The method of claim 7 wherein said label is a substrate for an enzyme.

9. The method of claim 8 wherein said enzyme is capable of acting on said substrate label to produce a detectable product.

10. The method of claim 9 wherein said detectable product is fluorescent.

11. The method of claim 7 wherein said label is a prosthetic group of an enzyme, said groups being capable of combining with an apoenzyme to form said enzyme.

12. The method of claim 11 wherein said label comprises flavin adenine dinucleotide and said apoenzyme is apoglucose oxidase.

13. The method of claim 1 wherein difference is the appearance of or a change in color.

14. The method of claim 1 wherein said difference is the appearance of or a change in chemiluminescence.

15. The method of claim 1 wherein said difference is the appearance of or a change in fluorescence.

16. The method of claim 1 in which said difference is the appearance of or change in fluorescence, chemiluminescence, phosphorescence, light absorption, light reflectance or color.

* * * * *